United States Patent [19]

Isono

[11] Patent Number: 4,469,416
[45] Date of Patent: Sep. 4, 1984

[54] AUTOMATIC FOCUSING MEANS FOR AN OPHTHALMOSCOPIC INSTRUMENT

[75] Inventor: Masaru Isono, Tokyo, Japan

[73] Assignee: Tokyo Kogaku Kikai Kabushiki Kaisha, Japan

[21] Appl. No.: 370,491

[22] Filed: Apr. 21, 1982

[30] Foreign Application Priority Data

Apr. 24, 1981 [JP] Japan ................................. 56-62964
Jan. 25, 1982 [JP] Japan ................................. 57-9705

[51] Int. Cl.³ .......................... G03B 3/00; G03B 29/00
[52] U.S. Cl. ....................................... 351/206; 354/62
[58] Field of Search ............... 351/206, 207, 208, 210; 354/162

[56] References Cited

U.S. PATENT DOCUMENTS 3,925,793  12/1975  Matsumura et al. ............ 351/206 X Primary Examiner—John K. Corbin
Assistant Examiner—Rodney B. Bovernick
Attorney, Agent, or Firm—Brumbaugh, Graves, Donohue & Raymond

[57] ABSTRACT

An ophthalmoscopic instrument includes a main optical system, with a focusing optical device, for producing an image of the fundus of an eye on an imaging plane, on illuminating optical system for illuminating the fundus, and a target projecting optical system for producing images of a plurality of target marks on the fundus. A photoelectric sensor produces electrical signals based upon the images of the target marks formed on the fundus, and the signals are processed to determine the distances between the images of the target marks. The instrument further includes a circuit for receiving the electrical signals based upon the images of the target marks and discriminating between these electrical signals and anomalous signals, a circuit for controlling the focusing optical device based upon information concerning the distances between the images of the target marks, and a circuit for restricting the focusing optical device when an anomalous signals is detected.

12 Claims, 21 Drawing Figures

FIG. 10
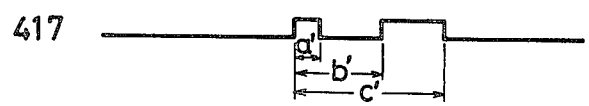
FIG. 11
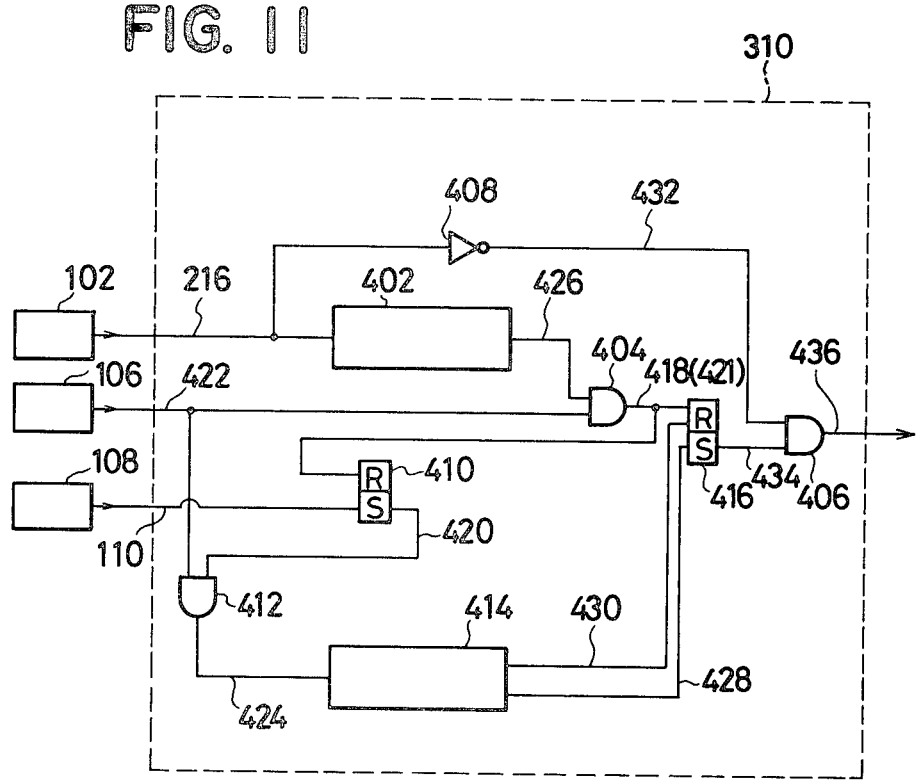

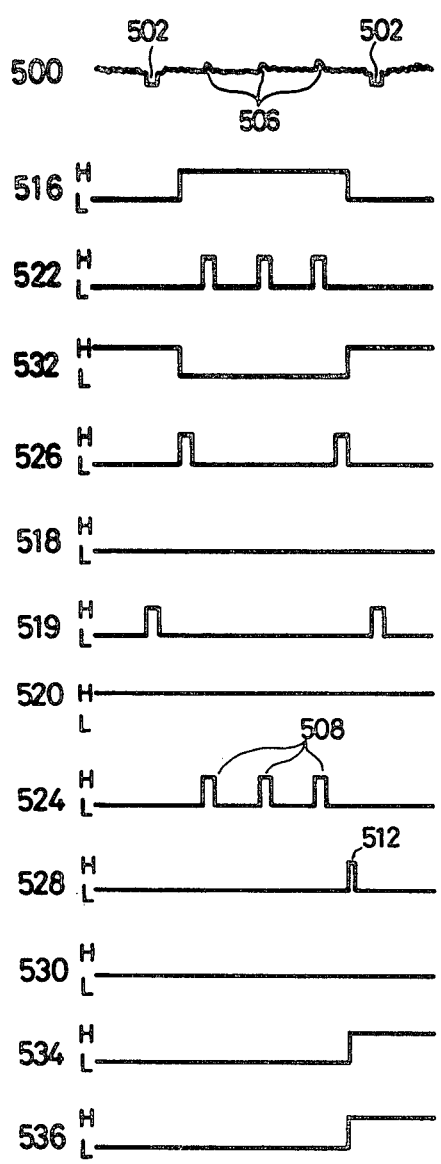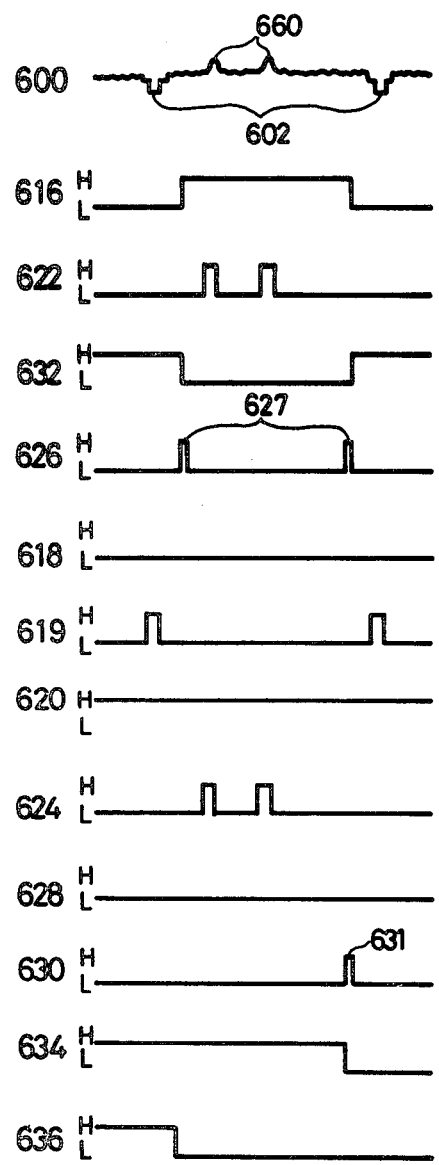

AUTOMATIC FOCUSING MEANS FOR AN OPHTHALMOSCOPIC INSTRUMENT

The present invention relates to an ophthalmoscopic instrument and more particularly to automatic focusing means for an ophthalmoscopic instrument.

In ophthalmoscopic instruments such as eye fundus cameras or eye refratometers, it is important to have the optical system focused on a patient's eye. Hithertofore, focusing has been carried out for example in an eye fundus camera by visually observing the image of the fundus of the patient's eye, however, such visual observation has not been satisfactory for accomplishing a correct focusing. It has therefore been proposed to provide means for projecting a target on the patient's eye fundus in such a manner that the image of the target is splitted unless the optical system is correctly focused. Further, proposals have also been made to provide an ophthalmoscopic instrument with an automatic focusing system in which a projected target image is detected to provide an electrical signal which is used to drive a focusing optical element in the optical system to establish a correct focusing.

In such automatic focusing system, it is essential for accomplishing a correctly focused condition to produce a clear image of the target on the patient's eye fundus, which is detected through the observing optical system of the instrument. It is however unavoidable to have target images which are not sufficiently clear due to blotting of the target image. Therefore, complicated operations are required to establish focusing based on such unclear informations.

There are several ways of projecting the target on the fundus of a patient's eye. For example, the target may include three marks which are so arranged that they do not align with each other when the optical system is not focused on the patient's eye fundus but they align under a focused condition. However, in this type of target, the images of the target marks become unclear due to blotting and fading at the eye fundus of the target image so that the target mark images are undistinguishable with each other when they come close to each other. This will limit the operable range of the automatic focusing device. It should further be pointed out that the conventional automatic focusing system may sometimes become inoperative in that the focusing lens is returned to the basic position which is the focused position in case where the patient's eye is a regular one, so that when the patient's eye is of a strong near or far sight two target mark images come very close to each other and become undistinguishable.

It is therefore an object of the present invention to provide automatic focusing means for an ophthalmoscopic instrument which is designed to perform automatic focusing based on distances of images of target marks projected on the patient's eye fundus but can discriminate anomalous signals which may be caused some kind of unusualness in the image detecting system.

Another object of the present invention is to provide automatic focusing means in which automatic focusing is performed by detecting distances of images of target marks and which has means for counting number of the target mark images and discriminating informations which do not contain a correct number of signals so that such informations are not used in automatic focusing operation.

A further object of the present invention is to provide automatic focusing means which includes means for discriminating information obtained when the patient's eye has blinked.

Still further object of the present invention is to provide automatic focusing means in which operable range can be increased.

According to the present invention, the above and other objects can be accomplished by an ophthalmoscopic instrument including a main optical system having focusing optical means and adapted for producing an image of a patient's eye fundus on an imaging plane, an illuminating optical system having light source means and adapted for illuminating the patient's eye fundus, a target projecting optical system having a plurality of target marks and adapted for producing images of said target marks on said eye fundus, photoelectric means for producing electric signals based on the images of the target marks formed on the eye fundus, means for receiving said electric signals and detecting distances between the images of the target marks, means for receiving said electric signals and detecting contrast between the signals to discriminate anomalous signals, focus control means for controlling the focusing optical means under informations based on the distances between the target mark images detected by the distance detecting means, means for restricting the focus control means when said contrast detecting means detects the anomalous signal. The contact detecting means may include means for counting number of the electric signals representing the images of the target marks and discriminating the anomalous signals when the number is not a predetermined one. Further, the contrast detecting means may include means for detecting changes in the electric signals due to blinking of the patient's eye.

The target marks may be constituted by three parallel lines. The main optical system may include optical means which makes it possible to observe the eye fundus as well as the images of the target marks on the eye fundus by producing observing images on said image plane and the photoelectric means includes means for sensing the observing images produced by the optical means.

The above and other objects and features of the present invention will become apparent from the following descriptions of preferred embodiments taking reference to the accompanying drawings, in which;

FIG. 2 (b) is a plan view of the target shown in FIG. 2 (a);

Figure 6:
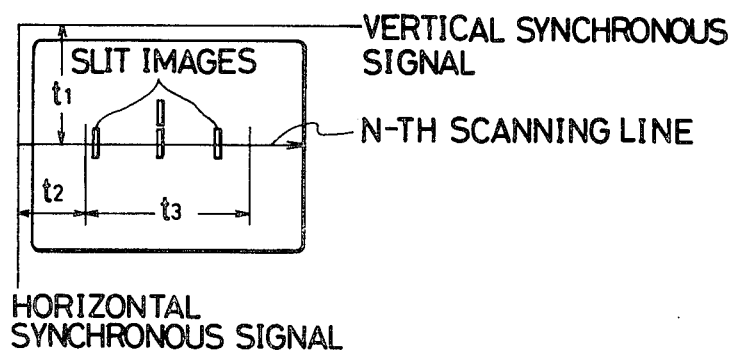
Figure 6:
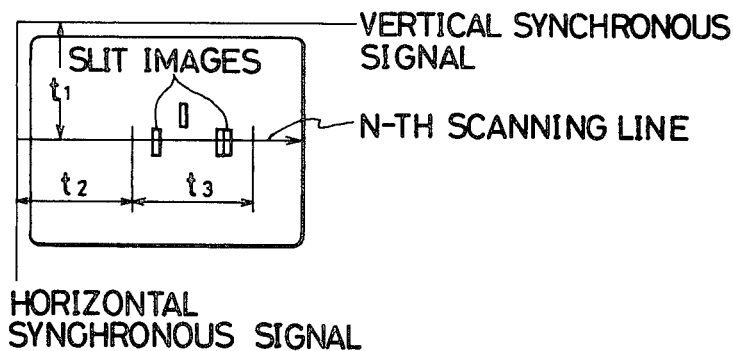
Figure 7:
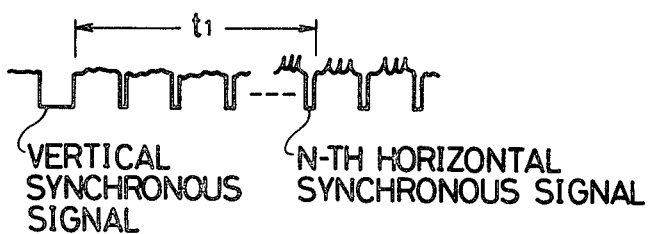
Figure 7:
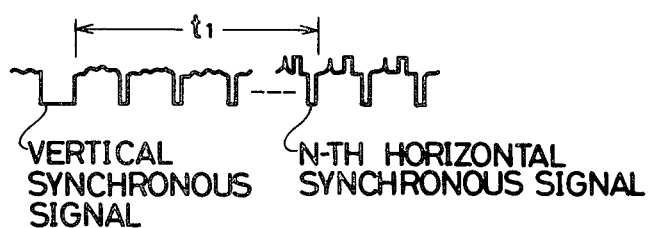
Figure 8:
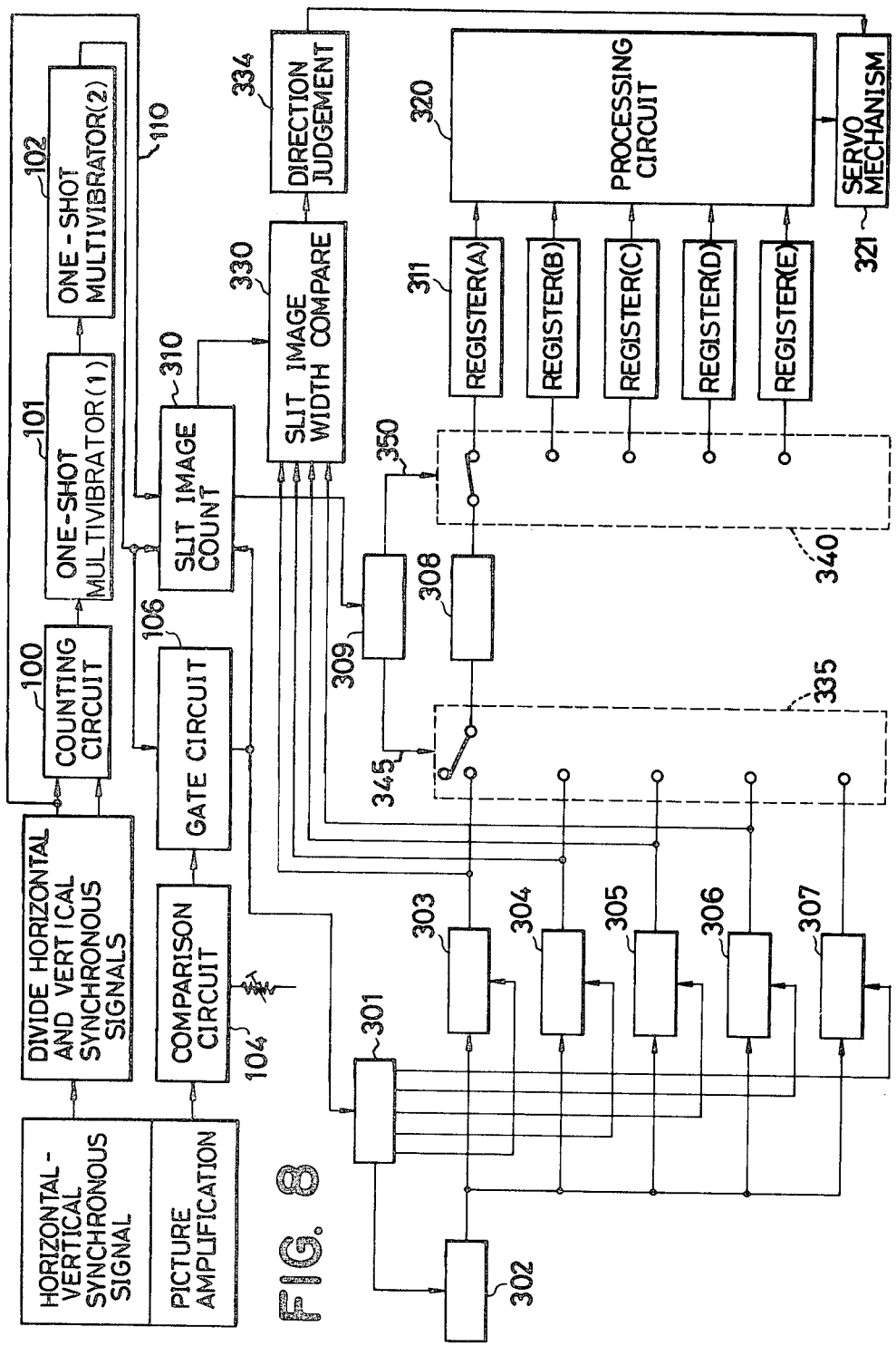
Figure 9:
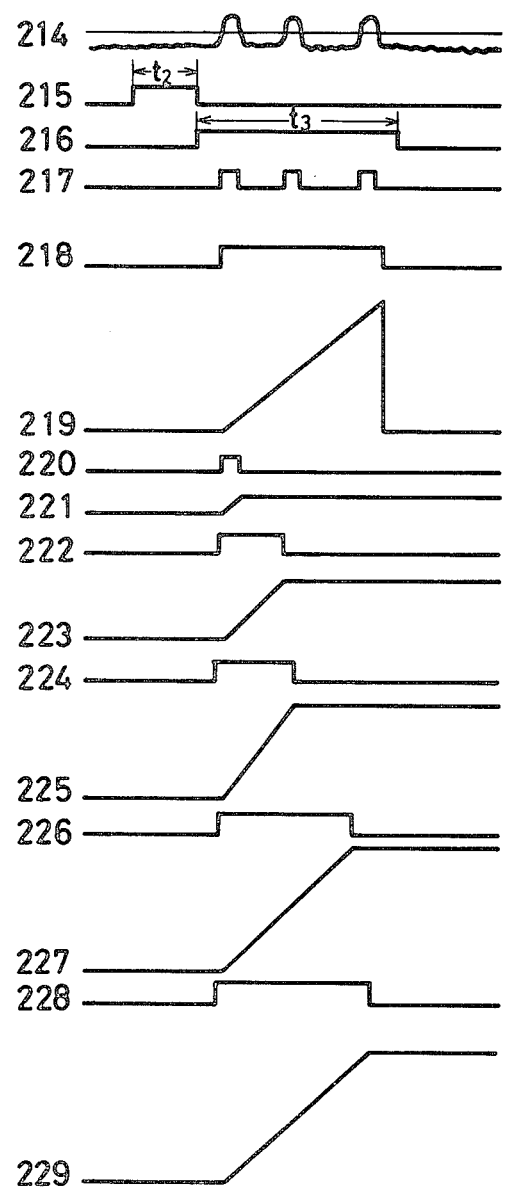
Figure 14:
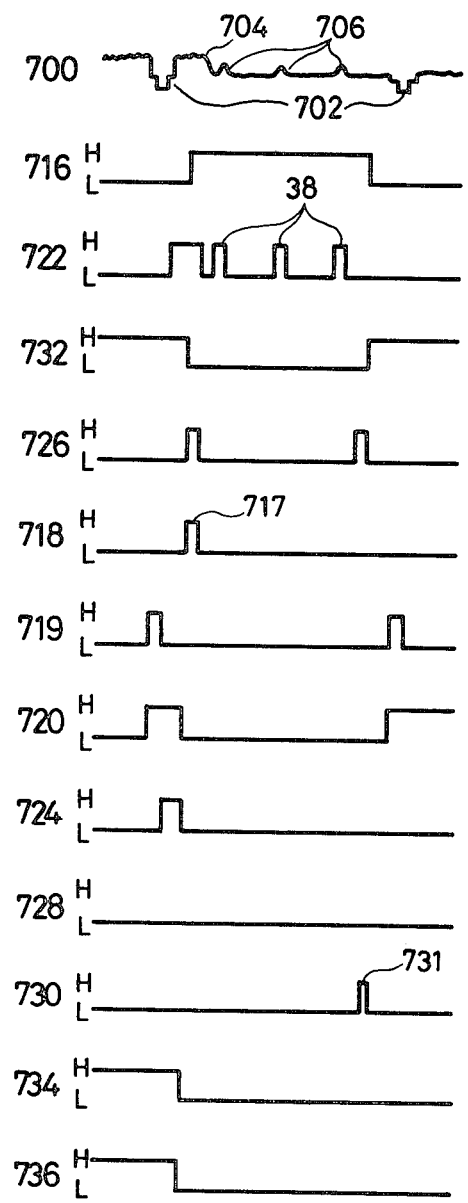

FIGS. 5 (a), (b), (c), (d) and (e), show the target images under various focusing conditions;

FIGS. 6 (a) and (b) show the relationship between the focusing condition and the target image;

FIGS. 7 (a) and (b) show patterns on a monitoring TV;

FIG. 8 is a block diagram showing the automatic focus control circuit in accordance with one embodiment of the present invention;

FIGS. 9 and 10 show wave patterns in various parts in the circuit shown in FIG. 8;

FIG. 11 is a block diagram showing a blink detecting circuit in accordance with one embodiment of the present invention; and FIGS. 12 through 14 show wave patterns in various parts in the circuit shown in FIG. 11.

The present invention will now be described with reference to the accompanying drawings.

Figure 1:
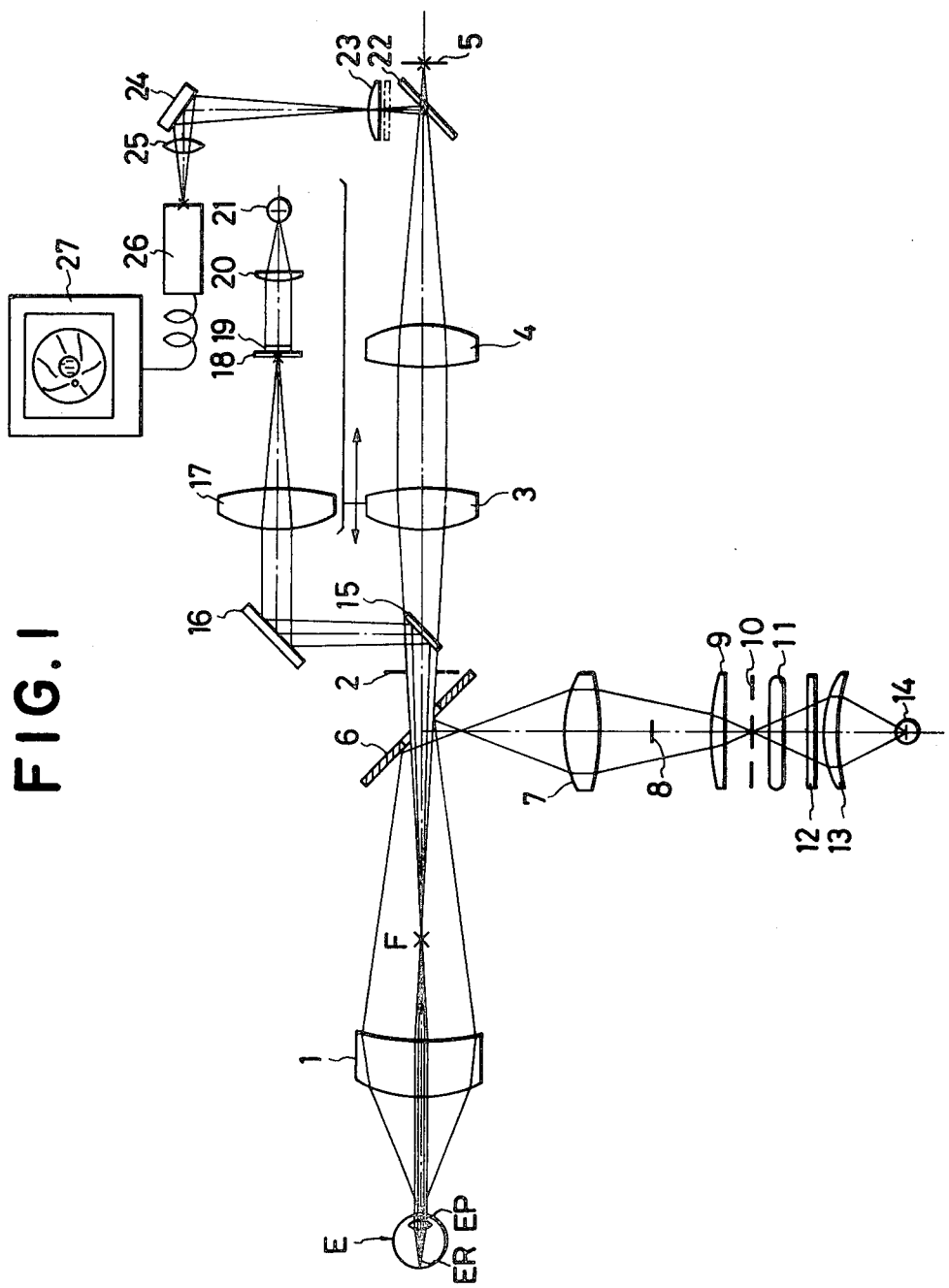
FIG. 1 is a diagrammatical illustration of an eye fundus camera.

Referring first to FIG. 1, a main or taking optical system comprises an objective lens 1 disposed with a working distance against an eye to be examined E, a diaphragm 2 located near a position conjugate from the pupil $E_p$ of the eye to be examined with respect to the objective lens 1, a focusing lens 3, an imaging lens 4 and a film. An afocal optical system is defined between the focusing lens 3 and the imaging lens 4. The object is imaged on the photoelectric surface of an image pickup tube 26 through a reflecting mirror 22 located slantwise at a position forwardly of the film 5, a field lens 23, a reflecting mirror 24, and an imaging lens 25, the latter three being disposed in the reflection optical path of the above reflecting mirror 22. Signals from the image pickup tube 26 are transmitted to a monitoring television set 27 in which an image is formed on the screen of a Braun tube.

An illuminating optical system comprises a perforated mirror 6 located slantwise in the optical path of the taking optical system at a position forwardly of the diaphragm 2, a relay lens 7, a condenser lens 9, a ring-shaped slit 10, a flash lamp 11 used as a source of light for taking, a heat-shielding filter 12, a condenser lens 13 and a source of light 14 for providing an ordinary illumination. All the components except the perforated mirror 6 are disposed in the reflection optical path of the perforated mirror 6. The illuminating light from the light source 14 is reflected by the perforated mirror 6 in the form of a ring and then passes through the objective lens 1 toward the fundus of the eye for illuminating it.

Figure 2A:
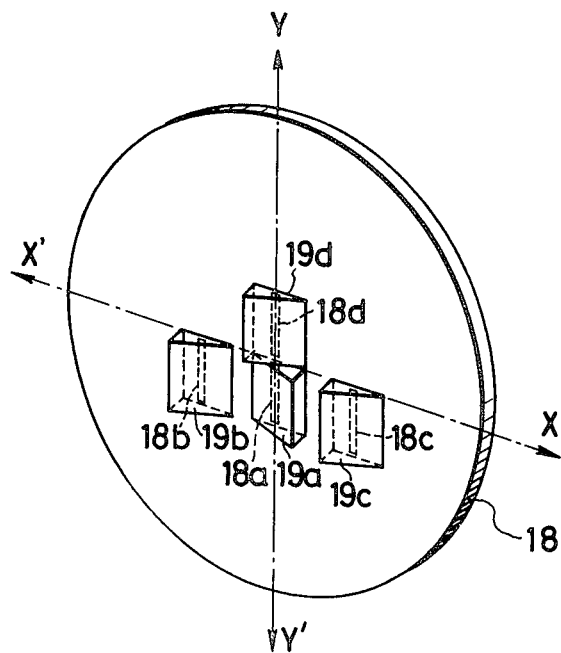
FIG. 2 (a) is a perspective view of a target used in one embodiment of the present invention.
Figure 2B:
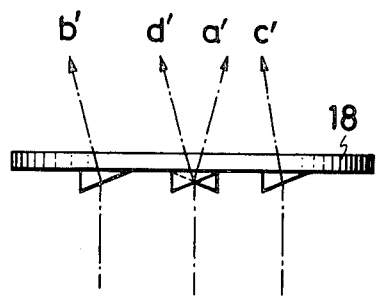

An index projecting system is provided to effect focusing in taking the photographic picture of the eyeground. This system comprises a reflecting mirror 15 located slantwise in the optical path of the taking optical system at a position rearwardly of the diaphragm 2, a reflecting mirror 16, a relay lens 17, a slit-shaped index 18, a deflection angle prism 19 disposed in close proximity to the index 18, a condenser lens 20 and a light source 21. Light from the source 21 passes through the condenser lens 20 toward the slit-shaped index 18 for illuminating it. As shown in FIG. 2a, the slit-shaped index 18 includes slit-shaped index sections 18a and 18b positioned on the Y—Y' axis, and slit-shaped index sections 18b and 18c positioned respectively parallel to the index sections 18a and 18d and spaced away from each other on the opposite sides of the X—X' axis at the same distance. Deflection angle prisms 19b, 19c and 19d are disposed over the slit-shaped index sections 18a, 18b, 18c and 18d, respectively. These prisms 19a, 19b, 19c and 19d respectively provide deflection angles in directions a', b', c' and d' in a plane including the X—X', as shown in FIG. 2b. Light passed through each of the slits is once imaged on a position F conjugate to the film 5 with respect to the lenses 3 and 4 through the relay lens 17, the reflecting mirror 16 and 15, the diaphragm 2 and the opening of the perforated mirror 6, and then incident on the eye to be examined E through the objective lens 1.

Figure 3:
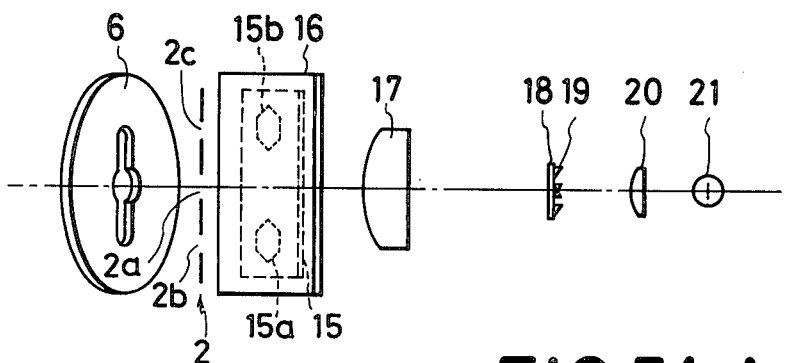
FIG. 3 is a diagrammatical illustration of a target projecting optical system.

In order to assure that a slit passing light split by the deflection angle prism 19 into two parts and projected symmetrically with respect to the optical axis is reflected toward the objective lens 1, the reflecting mirror 15 disposed in the optical path of the taking optical system includes two reflector sections 15a and 15b located symmetrically on the opposite sides of the optical axis, as shown in FIG. 3. Accordingly, the reflecting mirror 15 provides no obstacle to any effective light beam which has been reflected toward the film 5 at the eyeground $E_R$ in the taking optical system. In order to assure that the diaphragm 2 also permits for the taking light beam along the optical axis of the taking optical system and the slit passing light beams to pass therethrough, the diaphragm 2 includes a central aperture 2a for the taking light beam and apertures 2b and 2c located on the opposite sides of the central aperture for the split passing light beams. Furthermore, the opening of the perforated mirror 6 is provided with two elongations extending from the opposite sides thereof for permitting the slit passing light to pass therethrough.

It is desirable that the contrast in a slit index image projected onto the eyeground $E_R$ can be increased by blocking any background illumination at the projected area. For this end, the illustrated embodiment includes an insertable light-shielding plate 8 positioned at a position conjugate to the eyeground $E_R$ in the illumination system and having a size sufficient to block only the index image.

In the optical system shown in FIGS. 1 and 2, the focusing lens 3 is moved along the optical axis, in one united body, together with a unit consisting of the relay lens 17, the slit-shaped index 18, the deflection angle prism 19, the condenser lens 20 and the light source 21 in the index projecting system. Thus, focusing will be carried out to know the state of a slit-shaped index image formed on the eyeground $E_R$ and thus an image on the film 5.

Figure 4:
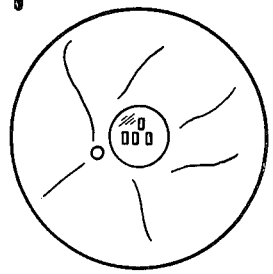
FIG. 4 is a view of a patient's eye fundus with a target image projected thereon.
Figure 5A:
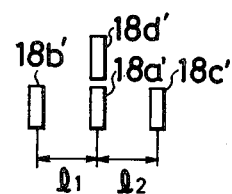
Figure 5B:
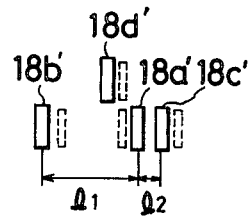
Figure 5D:
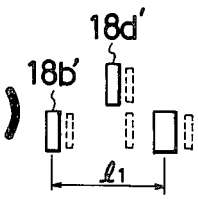
Figure 5C:
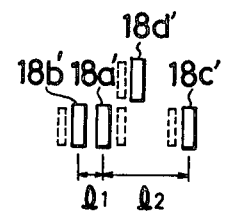
Figure 5E:
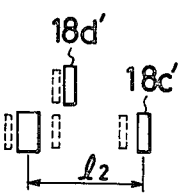

In such an arrangement, the monitoring TV set 27 displays the image of an eyeground as well as index images placed on the eyeground image, as shown in FIG. 4. When the eyeground of an eye to be examined is focused, the monitoring TV set 27 displays the slit-shaped index images 18a', 18b' and 18c' placed on the eyeground image in such a state that the index images are spaced away from one another at the same interval, as shown in FIG. 5a. When the eyeground image is placed slightly out of focus, the spacing $l_1$ between the slit-shaped index images 18a' and 18b' is not equal to the spacing $l_2$ between the index images 18a' and 18c', as shown in FIG. 5b or 5c. When the out-of-focus state in the eyeground image is further increased, the slit-shaped index image 18a' contacts with the slit-shaped index image 18b' or 18c' to form a slit-shaped index image increased in width, as shown in FIG. 5d or 5e. By electrically detecting these variable spacings $l_1$ and $l_2$, the direction of motion in the focusing lens 3 is determined depending on a positive or negative subtracter when the detected spacing $l_2$ is subtracted from the detected spacing $l_1$ ($l_1 - l_2$). If the spacing $l_1$ is equal to the spacing $l_2$, it is found that a focusing is properly attained. In the illustrated embodiment, the focusing state can be determined even by the operator's own eyes. If the slit-shaped index images 18a' and 18d' are aligned with each other on the same straight line, it would be known that the focusing state is attained. In such a manner, the visual determination of focusing state can be utilized instead of the aforementioned automatic focus detecting arrangement so that any re-taking will not be required even if there is any failure in the automatic focus detecting arrangement.

The above spacings $l_1$ and $l_2$ can electrically be detected by a method in which an index image is formed on a photo-diode array having light-receiving surfaces of very small area or an array consisting of charge coupled elements from which signals are used to determine the positions of the formed index images or by another method in which slit-like apertures forward of a photoelectric detector are scanned at a position in which slit-shaped index images are formed, signals from the photoelectric detector being used to determine the positions of formed index images. The illustrated embodiment will described with reference to a method in which an automatic focusing function is performed by utilizing television video scan signals to determine index image positions.

FIGS. 6a and 7a illustrate index images displayed on the screen of the monitoring TV set and a timing at which image signals are extracted, respectively. That is, n-th scan signal from a vertical synchronizing signal after time $t_1$ is extracted, and then signals are extracted for time $t_3$ from a point which is delayed from the n-th horizontal synchronizing signal by time $t_2$. These extracted signals are used to determine the positions of index images.

FIG. 8 is a block diagram of a circuit for automatically focusing by processing signals from the monitoring TV while FIG. 9 shows a waveform of each signal. A composite electric signal is separated into a horizontal-vertical synchronizing signal and an image signal. The horizontal-vertical synchronizing signal is further divided into a horizontal synchronizing signal and a vertical synchronizing signal which are in turn inputted to a counting circuit 100. Further the divided horizontal synchronizing signal 110 is supplied to the image number counting circuit 310. The counting circuit 100 is adapted to select the n-th scan signal delayed from the vertical synchronizing signal by time $t_1$ to generate a pulse when the horizontal synchronizing signals are counted up to n in number. At this timing, the first and second one shot multivibrators 101 and 102 generate signals 215 and 216, respectively. The vertical synchronizing signal resets the counting circuit 100 at each field. That is, the second one shot multivibrator 102 generates a gate signal 216 having a pulse width corresponding to time $t_3$ and being delayed from the n-th scan signal by time $t_2$. On the other hand, an image signal 214 is converted into a binary signal of H and L by means of a comparator 104 and inputted to a gate circuit 106 at which there is extracted a binary image signal 217 that is a binary signal converted by the gate signal 216 on the n-th scan line. Reference numeral 301 designates a timing signal generating circuit which generates timing signals 218, 220, 222, 224, 226 and 228. The timing signal 218 is supplied to a voltage generating circuit 302 while the timing signals 220, 222, 224, 226 and 228 are fed to sample holding circuits 303 to 307, repectively. The voltage generating circuit 302 produces a voltage 219 having a good linearity. The sample holding circuits 303 to 307 hold the voltage 219 respectively as 221, 223, 225, 227 and 229 under the action of the respective timing signal to obtain voltages having quantities of electricity which are required in scanning for the respective H periods. The sample holding circuits 303 to 306 are respectively coupled with the input of an index image width comparing circuit 330. The outputs of the above one-shot multivibrator 102 and gate circuit 106 are coupled with the input of an index image number counting circuit 310.

The index image number counting circuit 310 is adapted to count the number of output pulses (index image number) from the gate circuit 106 for a period in which the one shot multivibrator 102 produces output pulses. If the so obtained count, that is, index image number is equal to a predetermined number (three in the illustrated embodiment), the timing signal generating circuit 309 for selecting circuits receives at output an actuation signal. If the counted number is not equal to the above predetermined number, an actuation signal is supplied to the output of the index image width comparing circuit 330.

There will now be described such a case that the index images are formed on the eyeground in such a state as shown in FIG. 5b or 5c.

The timing signal generating circuit 309 for selecting circuits supplies the voltages held in the sample holding circuits 303 to 306 to an A/D converter 308 under the influence of actuation signals from the index image number counting circuit 310. In the A/D converter 308, the above voltages are converted into digital signals which are in turn stored in registers 311(A)–(E). An arithmatic circuit 320 serves to take in data from the registers (A)–(E) for determining the spacings $l_1$ and $l_2$ between the slit-shaped index images and then to provide signals with respect to amount and direction of movement to a servo-system 321 until the spacings are equal to each other. Where digital amounts stored in the registers (A)–(E) are respectively a, b, c, d and e, the spacing $l_1$ in FIG. 5 can be determined by the following equation:

$$l_1 = \frac{a}{2} + (b-a) + \frac{c-b}{2} = \frac{b-a+c}{2}$$

Similarly, the spacing $l_2$ can be obtained by the following equation:

$$l_2 = \frac{c-b}{2} + (d-c) + \frac{e-d}{2} = \frac{d-c+e-b}{2}$$

$\Delta l = l_1 - l_2$ represents an amount of movement while the positive or negative sign of $(l_1 - l_2)$ indicates a direction of movement. The servo-system 321 is actuated to move, in one united body, the focusing lens 3 together with the unit consisting of the relay lens 17, the slit-shaped index 18, the deflection angle prism 19, the condenser lens 20 and the light source 21 along the optical axis. Thus, the slit-shaped indexes can be focused on the eyeground so that the eyeground image will automatically be focused on the film 5.

There will now be described such a case that the slit-like index images 18a', 18b' and 18c' are formed markedly out of focus with each two index images being contacted with each other not to distinguish between these index images as shown in FIG. 5d or 5e. In this case, an image state and a timing at which image signals are extracted are as shown in FIGS. 6b and 7b, respectively. An image signal 415 is converted into a binary signal of H and L by means of a comparing circuit 104 as shown in FIG. 10. This binary signal is inputted to the gate circuit 106 at which a binary image signal 417 is extracted under the action of gate signal 216 on the n-th scan line. The index image number counting circuit 310 counts the number of binary image signals 417, that is, index images. If two index images are detected with the number reduced from the predetermined number only by one, an actuation signal is supplied to the index image width comparing circuit 330 which is in turn actuated to detect index image widths from the outputs of the sample holding circuits 303 to 306 and to determine the pulse widths a' and (c'−b') in the binary image signals, these values being compared with each other. If the difference between the values a' and (c'−b) is larger than a predetermined value, it is discriminated that two index images are contacted with each other to form a single index image as shown in FIG. 5d or 5e. As a result, the index image width comparing circuit 330 outputs a value a'−(c'−b') to a direction discriminating circuit 334. If the above difference is smaller than the predetermined value, the index image width comparing circuit 330 provides no output to the direction discriminating circuit 334 discriminates the sign of the value a'−(c'−b'), an output from the index image width comparing circuit 330 to generate at the output a control signal for determining the controlled direction in the servo-system 321. Under the influence of such a control signal, the servo-system moves the focusing lens in the desired direction so that the index images will be separated into three individual images. Thereafter, the spacings between three index images will be used to provide a focusing state.

Where the detection of three index images is not carried out due to any cause other than the case that two index images are in contact with each other to form a single index image, the index image width comparing circuit 330 provides no output signal to the direction discriminating circuit 334 so that the servo-system 321 cannot be actuated. This can avoid such an inconvenience that the focusing lens 3 and the relay lens 17 and others in the index projecting system are unnecessarily moved by the servo-system. The index image number counting circuit 310 comprises, as shown in FIG. 11, a blink or wink detection signal generating circuit 402 to which the gate signal 216 is inputted and an AND circuit 404 to which the output 426 of the wink detection signal generating circuit 402 and the binary image signal 422 of the gate circuit 106 are inputted. The output 418 of this AND circuit 404 is coupled with the reset terminal of a flip flop circiut 416 (hereinafter called F.F. circuit) and the reset terminal of a flip flop circuit 410 (hereinafter called F.F. circuit). If the eye to be examined winks, the output 418 of the AND circuit 404 includes a wink pulse 421 to reset the F.F. circuits 416 and 410. The set terminal of the F.F. circuit 410 receives image horizontal synchronizing signals 110 at each of which the F.F. circuit 410 is set. The output 420 of the F.F. circuit 410 is maintained at H-level until a wink pulse 421 is inputted to the reset terminal of the F.F. circuit 410. AND circuit 412 is provided to operate an AND between the binary image signal 422 and the output 420 of the F.F. circuit 410. The output 424 of the AND circuit 412 provides a signal of the same shape as the binary image signal 422 until the reset terminal of the F.F. circuit 410 is inputted by a wink pulse 421 indicative to a wink. The output 424 of the AND circuit 412 is coupled with the input of an index image number discriminating circuit 414 to cause it to count the number of index images. If a wink pulse 421 is supplied to the reset input terminal of the F.F. circuit 410, the output 424 of the AND circuit 412 outputs a signal L independently of the shape of image binary signal 422. As a result, the image binary signal 422 is not inputted to the index image number discriminating circuit 414 so that the number of index images will not be counted. The index image number discriminating circuit 414 is adapted to discriminate whether or not the number of counted index images corresponds to a predetermined value when the gate signal 216 is falling. If the number of counted index images is equal to the predetermined value, the index image number discriminating circuit 414 generates YES signal 428 in the form of pulse. If not, this circuit 414 produces NO signal 430 in the form of pulse. The YES signal 428 of this index image number discriminating circuit 414 is inputted to the set terminal of the F.F. circuit 416 while the NO signal 430 is inputted to the reset terminal of the same F.F. circuit. As a result, the F.F. circuit 416 is set by the YES signal 428 produced when the index image number discriminating circuit 414 has counted the number of index images up to the predetermined value, and reset by the NO signal 430 generated when the number of index images has not reached the predetermined value. NOT circuit 408 is provided to invert the gate signal 216 while AND circuit 406 is provide to operate "AND" between the output 432 of the NOT circuit 408 and the output 434 of the F.F. circuit 416. The output 436 of AND circuit 406 indicates L-level independently of the output 434 of the F.F. circuit 416 for a period that the gate signal 216 is in H-level, that is, that the output of the NOT circuit 408 is in L-level. If the gate signal 216 becomes L-level, the output signals 434 of the F.F. circuit 416 is counted. If the number of index images counted in the gate signals 216 is equal to a predetermined value, the F.F. circuit 416 will have its output 434 at H-level while at the same time the output 436 of the AND circuit 406 will also become H-level. On the other hand, if the number of counted index images is not equal to the predetermined number, the output of the F.F. circuit 416 becomes L-level while the output 436 of the AND circuit 406 also becomes L-level.

The output 436 of the AND circuit 406 is coupled with the input of a timing generating circuit 309 for selecting circuits. If the output 436 of the AND circuit 406 is in L-level, that is, if there is a wink pulse or no index image in the gate signal, the timing generating circuit 309 for selecting circuits is controlled by the AND circuit 406 to disable any focusing information obtained from index images. If the output 436 of the AND circuit 406 is in H-level, that is, if there is no abnormality such as wink in an eye to be examined, the above output 436 controls the circuit selecting and timing generating circuit 309 to make the focusing information obtained from index images effective.

The operation of the above arrangement will be described with reference to FIGS. 12, 13 and 14. FIG. 12 shows a timing chart in the operation of the abnormality detecting device 400 when there is no abnormality such as a wink or a lack of index image. In FIG. 12, 500 denotes a image signal from the pickup tube, which signal includes two recesses 502 indicating horizontal synchronizing signals of the monitoring TV set and three small protrusions 506 located near the center which are indicative of index images projected on the eye to be examined. The gate signal 216 defines a rectangular wave as shown by 516 and is inputted to the wink detection signal generating circuit 402 which in turn generates a wink detection pulse as shown by 526. "AND" of this signal 526 and a binary signal 522 from the image signal 500 is operated in the AND circuit 404 which in turn produces a signal 518 being at L-level at all times. This signal 518 is supplied to the reset input terminals of the two F.F. circuits 416 and 410. However, these F.F. circuits cannot be reset since there is no wink detection pulse. The set input terminal of the F.F.

circuit 410 receives the horizontal synchronizing signals 519 of the monitoring TV set so that the F.F. circuit will be set at each horizontal synchronizing signal 519. At this time, the output 420 of the F.F. circuit 410 becomes H-level as shown by 520 since no reset pulse is inputted to the reset terminal of the F.F. circuit 410 as described hereinbefore. As a result, the output of the AND circuit 412 which operates AND of the binary signal 522 and the output 520 of the F.F. circuit 410 defines a signal 524 of the same shape as that of the binary image signal 522. This signal 524 is inputted and counted to the index image number discriminating circuit 414 the input signal of which includes three binary index image pulses 508. The index image number discriminating circuit 414 compares the number of index images counted during falling of the gate signal 516 with a predetermined value (three). Since the number of counted index images of the input signal 524 is three corresponding to the predetermined number of three, YES output signal 428 will include an YES pulse 512 as shown by 528. NO output signal 430 does not produce NO pulse and defines a signal 530 being at L-level at all times. If the YES pulse 512 of YES signal 428 is inputted to the set terminal of the F.F. circuit 416, the output 434 thereof will become H-level as shown by 534. Further, AND circuit 406 is provided to operate "AND" of the output 434 of the F.F. circuit 416 and a signal 432 obtained by inverting the gate signal 216 by a inverter 408. The AND circuit 406 generates at output a signal 536 which rises to H-level from a point at which the gate signal 516 falls. The output 436 of the AND circuit 406 is coupled with the input of the timing generating circuit 309 for selecting circuits. Since the output of this AND circuit 406 becomes H-level. The circuit selecting and timing generating circuit 309 controls circuit selectors 335 and 340 by the circuit selecting and timing signals 345 and 350 thereof. The circuit selecting timing signal 345 is a control signal which causes the circuit selector 335 to successively connect the sample holding circuits 303 to 307 with an A/D converter 308. On the other hand, the circuit selecting timing signal 350 is a control signal which causes the circuit selector 340 to store the voltages of the sample holding circuits 303 to 307 in registers (A)-(E) after the voltages have been A/D converted by the A/D converter 308. Thus, the voltages held in the respective sample holding circuits as focusing information are stored in the registers (A)-(E). Data in the registers (A)-(E) are taken by an operational circuit 320 and then processed by a given operation. Thereafter, data is transmitted to a servomechanism as servo signals so that a unit consisting of the focusing lens 3, the relay lens 17, the slit-like indexes 18, the deflection angle prism 19, the condenser lens 20 and the light source 21 will be moved along the optical axis in one united body for focusing. If the index image number counting circuit 310 detects no abnormality, the servomechanism 321 carries out a determined focusing control based on the focusing information which is held in the holding circuits.

FIG. 13 shows a timing chart of the index image number counting circuit 310 when any index image lacks. 600 designates an image signal obtained from the image pickup tube which signal includes two recesses 602 indicative of horizontal synchronizing signals 110 of the monitoring TV set and two protrusions 606 located near the center which are indicative of index images projected on the eye to be examined. The gate signal defines a rectangular wave as shown by 616 and is inputted to the wink detection signal generating circuit 402 which in turn produces a signal 626 having wink detection pulses 627. "AND" of the signal 626 and a binary signal 622 from the image signal 600 is operated by the AND circuit 404. The output signal 618 of the AND circuit 404 is always placed at L-level without any wink detection pulse if there is no wink. The above output signal 618 is inputted to the reset terminals of two F.F. circuits 416 and 410. However, these F.F. circuits 416 and 410 will not be reset by this signal 618. The set terminal of the F.F. circuit 410 receives horizontal synchronizing signals 619 at each of which the F.F. circuit 410 is set. In this case, no reset pulse is inputted to the reset terminal of the F.F. circuit 410 so that the output 620 of the F.F. circuit 410 will be H-level at all times. Therefore, the output 424 of the AND circuit 412 which operates "AND" of the output 620 of the F.F. circuit 410 and the binary image signal 622 becomes a signal 624 of the same shape as that of the binary image signal 622. This signal 624 is inputted to the index image number discriminating circuit 414 for counting the number of index images. At this time, the binary image signal 622 includes two index images which does not correspond to the predetermined number of index images, that is, three. As a result, YES signal 428 of the index image number discriminating circuit becomes a signal 628 including no YES pulse which is in turn inputted to the set terminal of the F.F. circuit 416. On the other hand, NO signal 430 includes a NO pulse 631 and is inputted to the reset terminal of the F.F. circuit 416. The F.F. circuit 416 is reset by the NO pulse 631 with the output thereof being at L-level as shown by 634. The output 436 of the AND circuit 406 which operates "AND" of the output 634 of the F.F. circuit 416 and the inverted output 632 of the gate signal 616 becomes L-level. The output 436 of this AND circuit is inputted to the circuit selecting and timing generating circuit 309 so that the servomechanism 321 will not refer to the focusing information held in the sample holding circuits to effect the focusing in practice.

FIG. 14 shows a timing chart of the index image number counting circuit 310 when there is any wink in the eye to, be examined during detection of the focusing information. 700 denotes an image signal from the image pickup tube. This image signal 700 includes two recesses 702 formed on the opposite ends thereof which are indicative of horizontal synchronizing signals of the monitoring TV set, a relatively large protrusion 704 on the left-hand end indicating a reflected light which is produced by the wink of the eye to be examined, and three smaller protrusions 706 located near the center which are indicative of index images projected on the eye to be examined. The gate signal 216 is of a rectangular waveform as shown by 716 and inputted to the wink detection signal generating circuit 402 which in turn produces wink detection pulses as shown by 726. "AND" of this signal 726 and a binary signal 722 from the image signal 700 is calculated by the AND circuit 404. Since the reflected light produced by the wink is on the left-hand end of the signal 722, the wink detection pulse on the left-hand end of the output of the AND circuit 404 will not disappear to form a signal as shown by 718. The signal 718 is coupled with the reset input terminals of the F.F. circuits 410 and 416. The set input terminal of the F.F. circuit 410 receives horizontal synchronizing signals 702 at each of which the F.F. circuit 410 will be set. Accordingly, the F.F. circuit 410 is once set by the horizontal synchronizing signal 719 and then reset by the wink detection pulse 717 in the output 718 of the AND circuit 404 which has been inputted to the reset terminal of the F.F. circuit 410. As a result, the F.F. circuit 410 will not be again set unless the next horizontal synchronizing signal 719 is inputted to the set terminal thereof. The output of the F.F. circuit 410 becomes a signal 720. The AND circuit 412 operates "AND" of the output 720 of the F.F. circuit 410 and the binary image signal with the output thereof being of a signal 724 which includes only one pulse. This signal 724 is inputted to the index image number discrimination circuit 414. As a result, the index image number discrimination circuit 414 count one in the number of index images and thus discriminates that this count does not correspond to the predetermined number of three in comparison. The YES signal 428 of the index image number discrimination circuit then becomes a signal 728 having no YES pulse which is inputted to the set terminal of the F.F. circuit 416. NO signal 430 does not produce NO pulse 731 while a signal 730 is inputted to the reset terminal of the F.F. circuit 416. The F.F. circuit 416 is reset by the NO pulse 731. At this time, the output 434 thereof becomes L-level as shown by 734. The output 436 of the AND circuit 406, which operates "AND" of the output of the F.F. circuit 416 and the inverted output 632 of the gate signal 616 becomes L-level. Since the output 436 of the AND circuit is inputted to the circuit selecting and timing generating circuit 309, the servomechanism 321 will not refer to the focusing information held in the sample holding circuits so that any servo action cannot by carried out in practice.

The invention has thus been shown and described with reference to a specific embodiment, however, it should be noted that the invention is in no way limited to the details of the illustrated arrangements but changes and modifications may be made without departing from the scope of the appended claims.

I claim:

1. An ophthalmoscopic instrument including a main optical system having focusing optical means and adapted for producing an image of a patient's eye fundus on an imaging plane, an illuminating optical system having light source means and adapted for illuminating the patient's eye fundus, a target projecting optical system having a plurality of target marks and adapted for producing images of said target marks on said eye fundus, photoelectric means for producing electric signals based on the images of the target marks formed on the eye fundus, means for receiving said electric signals and detecting distances between the images of the target marks, means for receiving said electric signals and detecting contrast between the signals to discriminate anomalous signals, focus control means for controlling the focusing optical means under informations based on the distances between the target mark images detected by the distance detecting means, means for restricting the focus control means when said contrast detecting means detects the anomalous signal.

2. An ophthalmoscopic instrument in accordance with claim 1 in which said contrast detecting means includes means for counting number of the electric signals representing the images of the target marks and discrimating the anomalous signals when the number is not a predetermined one.

3. An ophthalmoscopic instrument in accordance with claim 2 in which said contrast detecting means includes means for detecting changes in the electric signals due to blinking of the patient's eye.

4. An opthalmoscopic instrument in accordance with claim 1 in which said target marks are constituted by three parallel lines.

5. An ophthalmoscopic instrument in accordance with claim 1 in which said main optical system includes optical means which makes it possible to observe the eye fundus as well as the images of the target marks on the eye fundus by producing observing images on said image plane and the photoelectric means includes means for sensing the observing images produced by the optical means.

6. An ophthalmoscopic instrument in accordance with claim 5 in which said main optical system further includes electrical means having a monitoring TV which makes it possible to visually observe images of the eye fundus and the target marks.

7. An ophthalmoscopic instrument in accordance with claim 6 in which said photoelectric means includes an image taking tube which produces electrical video signals.

8. An ophthalmoscopic instrument in accordance with claim 4 in which said photoelectric means includes scanning means for scanning images produced by said main optical system, said three lines constituting the target marks are arranged in parallel with each other in a direction of the scanning of said scanning means.

9. An ophthalmoscopic instrument including a main optical system having focusing optical means and adapted for producing an image of a patient's eye fundus on an imaging plane, an illuminating optical system having light source means and adapted for illuminating the patient's eye fundus, a target projecting optical system having a plurality of target marks and adapted for producing images of said target marks on said eye fundus, photoelectric means for producing electric signals based on the images of the target marks formed on the eye fundus, means for receiving said electric signals and detecting distances between the images of the target marks, means for receiving said electrical signals and detecting widths of the images of the target marks, counting means for receiving said electrical signals and counting number of images of the target marks, image discriminating means for comparing the number of the images of the target marks counted by the counting means with a predetermined number, focus control means for controlling focusing optical means in accordance with outputs from the distance detecting means when the number of the images of the target marks is equal to the predetermined number and in accordance with outputs from said width detecting means when the number of the images of the target marks is different from the predetermined number.

10. An ophthalmoscopic instrument in accordance with claim 9 in which said target marks are constituted by three parallel lines.

11. An ophthalmoscopic instrument in accordance with claim 10 in which said predetermined number is three and said focus control means controls the focusing optical means so that focusing operation is not performed when the number as counted by the counting means is not two and three.

12. An ophthalmoscopic instrument in accordance with claim 11 in which said focus control means includes means for comparing when the number as counted is twice the widths of two images of the target marks and performing the focusing operation when the width of one of the images is approximately two times as large as that of the other.

* * * * *